United States Patent [19]

Zhadanov

[11] Patent Number: 5,304,193

[45] Date of Patent: Apr. 19, 1994

[54] BLOOD LANCING DEVICE

[76] Inventor: Sam Zhadanov, 100 Prospect St., Metachin, N.Y. 08840

[21] Appl. No.: 105,131

[22] Filed: Aug. 12, 1993

[51] Int. Cl.⁵ ............................................. A61B 17/32
[52] U.S. Cl. ................................... 606/182; 606/185; 128/770
[58] Field of Search ............... 606/182, 183, 185, 188; 128/770; 604/136, 137, 138, 139, 157

[56] References Cited

U.S. PATENT DOCUMENTS

| | | | |
|---|---|---|---|
| Re. 32,922 | 5/1989 | Levin et al. | 606/182 |
| 4,469,110 | 9/1984 | Slama | 606/182 X |
| 4,924,879 | 5/1990 | O'Brien | 606/182 X |
| 5,074,872 | 12/1991 | Brown et al. | 606/182 |
| 5,196,025 | 3/1993 | Ranalletta et al. | 606/182 |

*Primary Examiner*—Michael H. Thaler
*Attorney, Agent, or Firm*—Ilya Zborovsky

[57] ABSTRACT

A blood lancing device for puncturing a skin has a lancet longitudinally displaceable in a first direction to puncture a skin of a patient and then into a second opposite direction out of the punctured skin, a spring having an active stroke, a toothed rack displaceable by the spring during its active stroke in the first direction; a toothed pinion engageable with and rotatable by the toothed rack when it moves in the first direction, and a lever having a first end connected with the toothed pinion and a second end connected with the lancet so that during the rotation of the pinion under the action of displacement of the toothed rack caused by the spring the second end of the lever moves the lancet successively in the first direction and in the second direction.

13 Claims, 1 Drawing Sheet

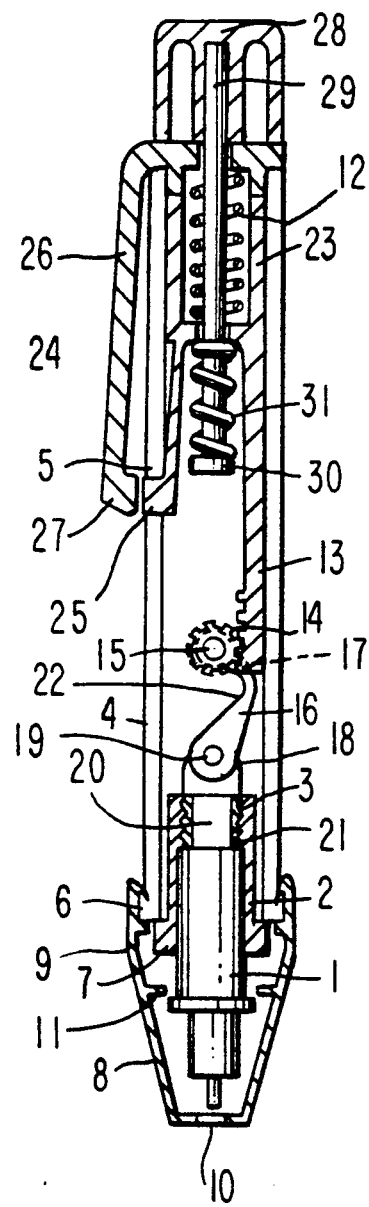

BLOOD LANCING DEVICE

BACKGROUND OF THE INVENTION

The present invention relates to a blood lancing device used for punturing a skin of a fingertip, preferably for home use.

Blood lancing devices are known in the art. A known blood lancing device has a lancet and a mechanism for its movement in two opposite longitudinal directions so as to puncture the skin of a patient and then to withdraw the lancet from the punctured skin. The known mechanisms have some disadvantages in that during their operation the lancet is subjected to vibrations and chatter which results in pain inflicted to the patient. Some attempts have been made to reduce the vibrations and chatter; however, further improvements are desirable in this sense.

SUMMARY OF THE INVENTION

Accordingly, it is an object of the present invention to provide a blood lancing device which is a further improvement of existing devices of this type.

In keeping with these objects and with others which will become apparent hereinafter, one feature of the present invention resides in a blood lancing device in which a mechanism for longitudinal displacement of the lancet includes a toothed rack actuatable by a spring which relaxes after being compressed, a pinion which is rotatable by the toothed rack, and a flexible lever having one end connected with the pinion snd another end connected with the lancet so that during the rotation of the pinion by the rack movable by the spring the lancet is displaced by the lever in two opposite directions to puncture the skin and to move back.

When the blood lancing device is designed in accordance with the present invention, the vibration and chatter of the lancet are essentially eliminated due to very smooth reversal of the lancet movement and thereby pain during the lancet penetration is substantially reduced.

The nove features of the present invention are set forth in the appended claims. The invention itself, however, both as to its construction snd its manner of operation will be best understood from the following description of preferred embodiments, which is accompanied by the following drawings.

BRIEF DESCRIPTION OF THE DRAWINGS

The single FIGURE of the drawings is an elevational view of a blood lancing device in accordance with the present invention, in section along a central longitudinal plane.

DESCRIPTION OF PREFERRED EMBODIMENTS

A blood lancing device in accordance with the present invention has a lancet which is identified with reference numeral 1 and is known per se. The lancet 1 is held in a lancet holder 2, in particular in an inner opening of the latter under the action of friction between two cooperating surfaces of the former and the latter. The lancet holder 2 has a rear narrower opening portion provided with an inner thread 3.

The device further has a housing 4 having a lateral slot 5. The housing 4 has a lower end provided with a flange 6 which cooperates with a flange 7 of the lance holder 2. The opening of the lower end of the housing 4 is closed by a hood 8 having a rear end 9 releasably engageable with the flange 6 of the housing, for example by a bayonet lock. The hood is substantially closed and has a central front opening 10. Preferably, the hood has the shape of a cone which narrows toward the opening 10. In the interior the hood has an annular projection 11 which is elastically yieldable in direction toward the opening 10 but rigid in the opposite direction, for example due to its concavity away from the opening.

A compression spring 12 has an active, relaxation stroke downwardly so as to displace the lancet 1 during its active stroke also downwardly in order to pierce a skin of the patient. The active stroke of the spring 12 is directly applied to a toothed rack 13 which has teeth engaging with teeth of a toothed pinion 14. The latter is rotatably mounted on an axle 15 which for example rotates in corresponding receiving openings of the housing. The device further has a lever 16 having a first leg 17 which is connected with the pinion 14, for example by fixed connection to the axle 15. Its another leg 18 is pivotally connected with a member 20 through a pivot point 19. The member 20 has an outer thread 21 with which it is screwable into the thread 3 of the threaded opening of the lancet holder 2. The lever 16 is formed as a flexible lever due to for example a bending point 22 in its middle.

The rear end 23 of the toothed rack is cup-shaped and accommodates the spring 12. At the side opposite to the main portion of the toothed rack, the latter has an elongated projection 24 with an end tooth 25 engageable in and disengageable from the slot 5 of the housing 4. The projection 24 is formed so that it is spring-biased radially outwardly for providing the normal engagement of its tooth 25 into the slot 5. An actuating member 26 provided with a lower tooth 27 is made separate from the rear portion 23 of the toothed rack. The tooth 27 is located opposite to the tooth 25 and can push the latter out of the slot 5. The member 26 is spaced from the outer surface of the housing and is formed as a clip, so that a part of a clothes can be inserted between the clip and the housing to hold the device of the user's clothes.

The device further has an actuating knob 28 with a pin 29 extending into the interior of the device or more particularly through the rear part 23 of the toothed rack and having an end flange 30. A relatively weak spring 31 is located between the flange 30 and the lower surface of the rear part 23 of the toothed rack.

The blood lancing device in accordance with the present invention operates in the following manner.

In the position shown in the drawing the lancet 1 is completely confined inside the lance holder 2 in the hood 8. To activate the device, the user pushes the clip 26 radially inwardly and its tooth 27 presses the tooth 25 of the projection 24 inwardly and out of the engagement with the slot 5 of the housing. The spring 12 is immediately relaxed and displaces the toothed rack 13 downwardly in the drawing so that the latter rotates the toothed pinion 14. During the rotation of the toothed pinion the lever 16 is turned from the bent position shown in the drawings first to a straightened position so that it extend vertically, and during the turning displaces downwardly the member 20, the lancet holder 2 and thereby the lancet 1. When the lever 16 is straightened, the lancet 1 punctures the skin of a patient. Then the toothed rack 13 continues to move downwardly and the toothed ponion 14 continues to rotate, causing the lever 16 to bend in an opposite direction so as to again reduce the distance between 15 and 19 and thereby to pull the member 20, the lancet holder 2 and the lancet 1 upwardly to withdraw the lancet 1 from the skin. During the whole process the lancet 1 moves downwardly, reverses the direction of its movement in the lowermost point, and then moves upwardly in a continuous, smooth and vibration-free manner.

After the puncturing the hood 8 can be removed from the housing together with the lancet 1 which is held inside the hood by the projection 11, and the lancet can be disposed if needed. The penetration depth of the lancet can be adjusted by screwing of the lancet holder 2 relative to the member 20, thus reducing or increasing the distance between the points 15 and 18 and thereby the stroke of the member 20, the lancet holder 2 and the lancet 1.

By pulling upwardly the knob 28 the toothed rack 13 is withdrawn rearwardly and the tooth 25 of the projection 24 again engages in the slot 5 of the housing. The spring 31 returns the knob to a position in which it abuts against the upper surface of the upper portion 23 of the toothed rack.

The present invention is not limited to the details shown since various modifications and structural changes are possible without departing from the spirit of the invention.

What is desired to be protected by Letters Patent is set forth in the appended claims.

I claim:

1. A blood lancing device, comprising
   a lancet longitudinally displaceable in a first direction to puncture a skin of a patient and then into a second opposite direction out of the punctured skin;
   spring means having an action stroke in said first direction;
   a toothed rack longitudinally displaceable in said first direction under the action of said active stroke of said spring means;
   a toothed pinion engageable with said toothed rack and rotatable by the letter during said longitudinal displacement of said toothed rack in said first direction;
   a lever having a first end connected with said pinion and a second end connected with said lancet so that during the rotation of said pinion by said toothed rack activated by said spring means said lever by said second end moves said lancet first in said first direction and thereafter in said second direction.

2. A blood lancing device as defined in claim 1, wherein said lever is flexible and has a bending point in the region between said first end and said second end so that during the rotation of said pinion said lever bends in said bending point.

3. A blood lancing device as defined in claim 1; and further comprising a lancet holder which holds said lancet, said second end of said lever being connected with said lancet holder so as to move the latter and thereby said lancet in said first and second directions.

4. A blood lancing device as defined in claim 3, wherein said second end of said lever is pivotally connected with said lancet holder; and further comprising means for pivotally connecting said second end of said lever with said lancet holder.

5. A blood lancing device as defined in claim 2; and further comprising penetration depth adjusting means including a first thread provided in said lancet holder and a member pivotally connected with said second end of said lever in a pivot point and having a second thread engageable with said first thread so as to displace said pivot point farther from or closer to said pinion.

6. A blood lancing device as defined in claim 1; and further comprising a housing accommodating a rear end of said lancet, said toothed rack, said toothed pinion and said lever, said housing having an opening through which a tip of said lancet extends; and a hood which is mountable on said housing so as to close said opening of said housing and surround a front end of said lancet.

7. A blood lancing device as defined in claim 6, wherein said hood is removable from said housing.

8. A blood lancing device as defined in claim 7, wherein said hood has an engaging formation which engages with said lancet and removes the latter from an interior of said housing when said hood is removed from said housing so that a tip of said lancet is confined in said hood and said lancet cannot be removed from said hood.

9. A blood lancing device as defined in claim 1; and further comprising means for retaining said spring means in an inactive position and then releasing said spring means so that the latter relax and move to said active position.

10. A blood lancing device as defined in claim 9; and further comprising a housing having a slot, said retaining and releasing means including a projection provided on said toothed rack and engaging in said slot so that said toothed rack retains said spring means in said inactive position, and an actuating member which pushes said projection out of said slot so that said spring means relax and obtain said active stroke.

11. A blood lancing device as defined in claim 10, wherein said actuating member is formed as a clip which is springy and extends outside said housing at a distance therefrom so that a part of a user's clothes can be inserted between said clip and said housing to hold the device on the user's clothes.

12. A blood lancing device as defined in claim 1; and further comprising means for retracting said toothed pinion to an inactive position and including a knob provided with an inner plunger engageable with said toothed rack, so that when a user pulls said knob in said second direction said toothed rack is withdrawn to its inactive position against the action of said spring means and the latter is compressed.

13. A blood lancing device as defined in claim 12; and further comprising means for returning said knob to its initial position and including a return spring acting on said knob.

* * * * *